(12) United States Patent
Torres et al.

(10) Patent No.: US 7,669,607 B2
(45) Date of Patent: Mar. 2, 2010

(54) INTERDENTAL SPACE CLEANER

(76) Inventors: Alma Torres, Urb. Santa Maria 124 Violeta, Rio Piedras, PR (US) 00927; Carlos Juan Rivera, Via 52 No. 4GS-5 Urb. Villa Fontana, Carolina, PR (US) 00983

( * ) Notice: Subject to any disclaimer, the term of this patent is extended or adjusted under 35 U.S.C. 154(b) by 302 days.

(21) Appl. No.: 11/810,128

(22) Filed: Jun. 5, 2007

(65) Prior Publication Data
US 2008/0302386 A1 Dec. 11, 2008

(51) Int. Cl.
*A61C 15/00* (2006.01)
(52) U.S. Cl. ........................ 132/329; 132/321
(58) Field of Classification Search ............... 132/321, 132/329
See application file for complete search history.

(56) References Cited

U.S. PATENT DOCUMENTS

| 725,081 | A | * | 4/1903 | Hills ........................... 132/329 |
| 1,462,062 | A | * | 7/1923 | Browning ................... 132/329 |
| 2,896,639 | A | * | 7/1959 | Fleming ..................... 132/321 |
| 5,415,276 | A | * | 5/1995 | Welton ....................... 206/104 |

FOREIGN PATENT DOCUMENTS

GB 2059266 A * 4/1981

* cited by examiner

*Primary Examiner*—Robyn Doan

(57) ABSTRACT

An interdental cleaning device that is easy to handle, especially for kids and handicapped people, including a frame supporting four zones for removing food and plaque between the teeth. Each zone having a particular thickness combined with cleaning substance and cleaning surface for a thorough teeth cleaning.

11 Claims, 6 Drawing Sheets

INTERDENTAL SPACE CLEANER

STATEMENT REGARDING FEDERALLY SPONSORED RESEARCH AND DEVELOPMENT

N/A

RELATED APPLICATIONS

N/A

BACKGROUND OF THE INVENTION

1. Field of the Invention

The present invention relates generally to an interdental space cleaner, and more particularly, to an easy to handle interdental cleaner having different cleaning zones.

2. Discussion of the Background

Regular and frequent regimen of teeth cleaning is required for a good oral hygiene. Several instruments such as the toothbrush are commonly used for that purpose. However some teeth areas are not properly cleaned by the toothbrush because of its design. Therefore, other devices such as toothpicks, dental floss and other dental instruments are provided for cleaning interdental spaces removing food and dental plaque preventing caries and inflammation of the gum.

The use of dental floss has been known for decades. Dental Floss is commonly used by adults rather than kids or even some handicap people having limited use of one hand. Therefore, even though is used often dental floss is unpopular, especially for kids, because it is necessary to be familiar with the application technique which requires time, patience and the use of both hands.

The conventional toothpicks, as mentioned above, are another choice for interdental cleaning mainly because of their cost. However the toothpick is difficult to use in areas where the teeth are really close together and does not maintain sufficient strength.

An example of a toothpick is U.S. Pat. No. 5,234,009 which discloses a toothpick made from plastic comprising an elongated body portion having an upwardly extending ridge and a pair of angulated legs defining a longitudinal groove. The tip end of the toothpick having different angles, however it not easy to be used by a kid or a handicapped person and also does not provide enough area to not just remove the food between the teeth but also clean the teeth by contact.

Accordingly, there is a need in the art for a dental cleaning device that is easy to handle, especially for a kid or a handicapped person, which not just removes the food between teeth but also encourage thorough teeth 10 cleaning to prevent carries and inflammation of the gum.

SUMMARY OF THE INVENTION

The present invention is a dental device having different thickness cleaning zones, which not just remove the food between the teeth but is easy to handle and also contact's the teeth for a thorough teeth cleaning.

Another object is to provide a dental cleaning device able to clean the different distances between the teeth properly.

Another object is to provide a dental cleaning device for handicapped people and kids that can be handled with just one hand.

Another object is to provide a dental cleaning device having a plurality of different cleaning zones easy to manufacture.

Another object is to provide a dental cleaning device with different cleaning zones.

Another object is to provide a dental cleaning device more attractive for the kids.

Another object is to provide a dental cleaning device which can be personalized to display information or for advertisement.

The invention itself, both as to its configuration and its mode of operation will be best understood, and additional objects and advantages thereof will become apparent, by the following detailed description of a preferred embodiment taken in conjunction with the accompanying drawing.

When the word "invention" is used in this specification, the word "invention" includes "inventions", that is, the plural of "invention". By stating "invention", the Applicant does not in any way admit that the present application does not include more the one patentable and non-obviously distinct invention and Applicant maintains that the present application may include more than one patentably and non-obviously distinct invention. The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

DESCRIPTION OF THE PREFERRED EMBODIMENT

Figure 1:
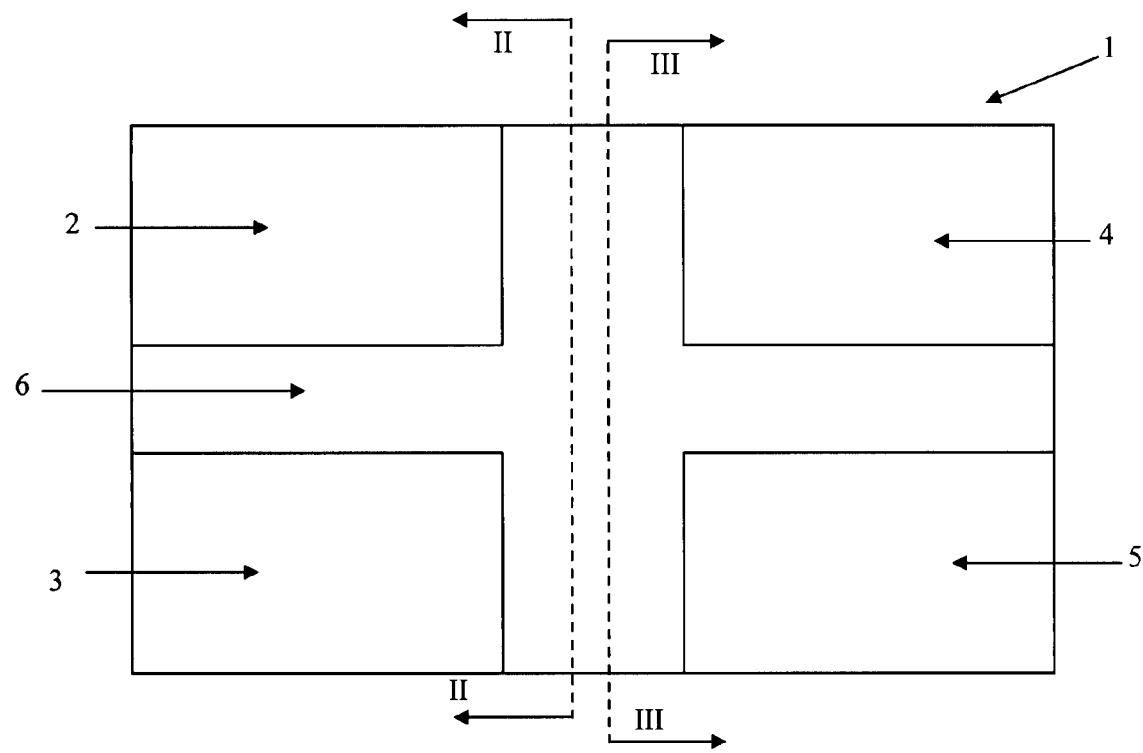
FIG. 1 is a top view of the interdental cleaner
Figure 2:
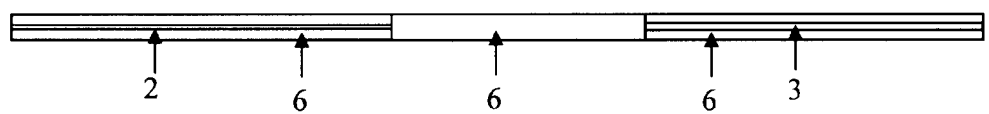
FIG. 2 is a cross section view on line II-II of the interdental cleaner
Figure 3:
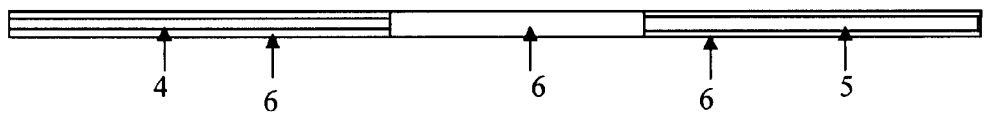
FIG. 3 is a cross section view on line III-III of the interdental cleaner

Referring to FIG. 1-FIG. 3, the preferred embodiment of the present invention shows an interdental cleaner 1 for removing food and dental plaque comprising four cleaning zones 2-5, wherein said cleaning zones 2-5 have different thickness and are supported by a frame 6. The zone thickness is between ranges of 0.003 mm and 0.018 mm, however the thickness disclosed is not intended to limit the invention since the thickness may vary. For example, the thickness may be customized depending on the customer's necessities.

As shown in FIGS. 1-3, the interdental cleaner 1 has a business card shape wherein the stiffness of frame 6 is greater or equal to higher stiffness zone since this portion gives support and rigidity to each zone. The frame 6 can be made of the same material as the zones or a different material as long the frame fulfill the stiffness requirements. In order to use the device the user holds with one hand 12 the interdental cleaner device 1 by the rigid frame 6 and depending on the space between teeth 10 he/she select's the flexible cleaning zone to be used. Depending on the thickness of the cleaning zone the easier will be the access between the teeth 10, however the thickness selected by the user should be the one that not just provides an easier access but also that has a greater contact with the teeth 10 in order to remove not just the food but also the plaque around the teeth 10. The frame thickness can be equal to the greater thickness of the zones, therefore making one of the zones thickness equal to the frame for an easier manufacture.

Figure 4:
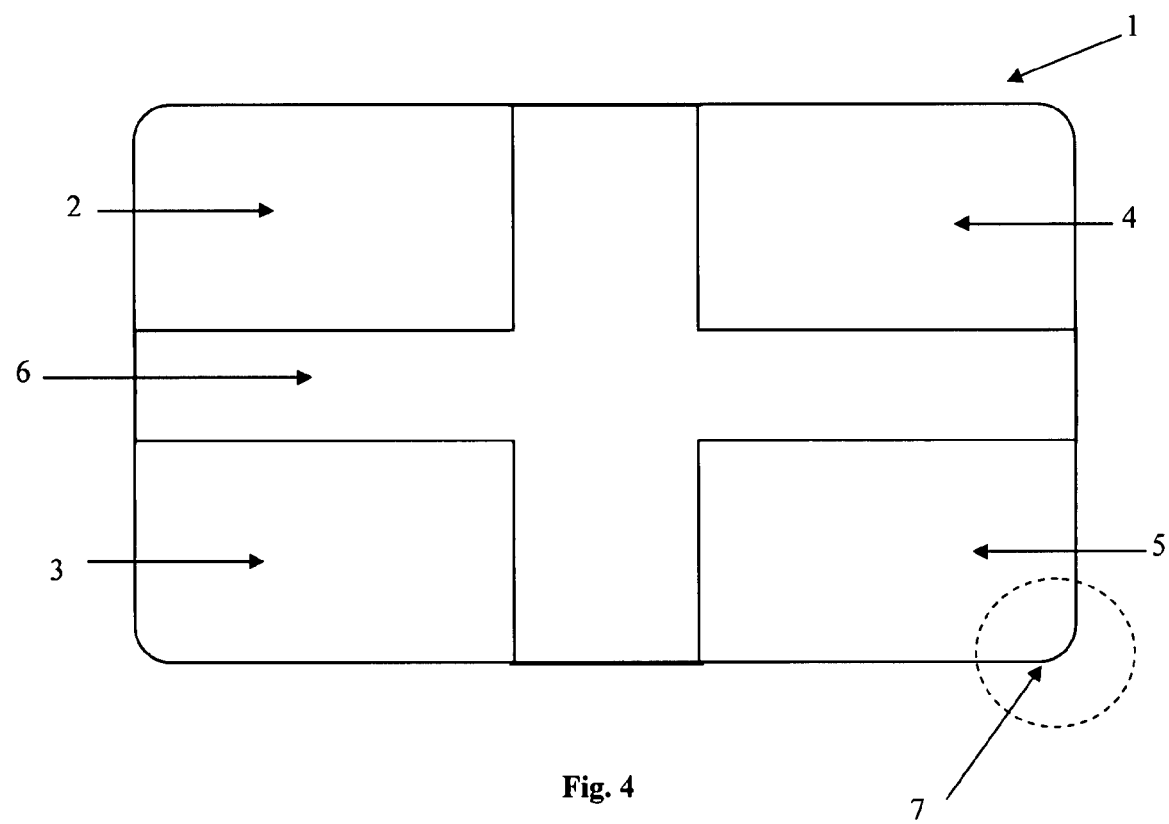
FIG. 4 is a top view of the second embodiment of the interdental cleaner.
Figure 5:
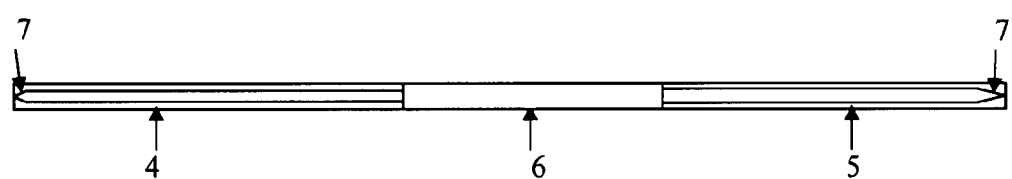
FIG. 5 is a side view of the second embodiment

FIG. 4 and FIG. 5 of the present invention disclose a second embodiment. As show in the preferred embodiment, the second embodiment is structurally similar providing four different zones 2-5 having different thickness, however in this embodiment each corner 7 is tapered in order to provide an easier access between teeth 10. The tapered portion 7 can be extended to the whole outer surface of the interdental device for a smoother interdental access.

Figure 6:
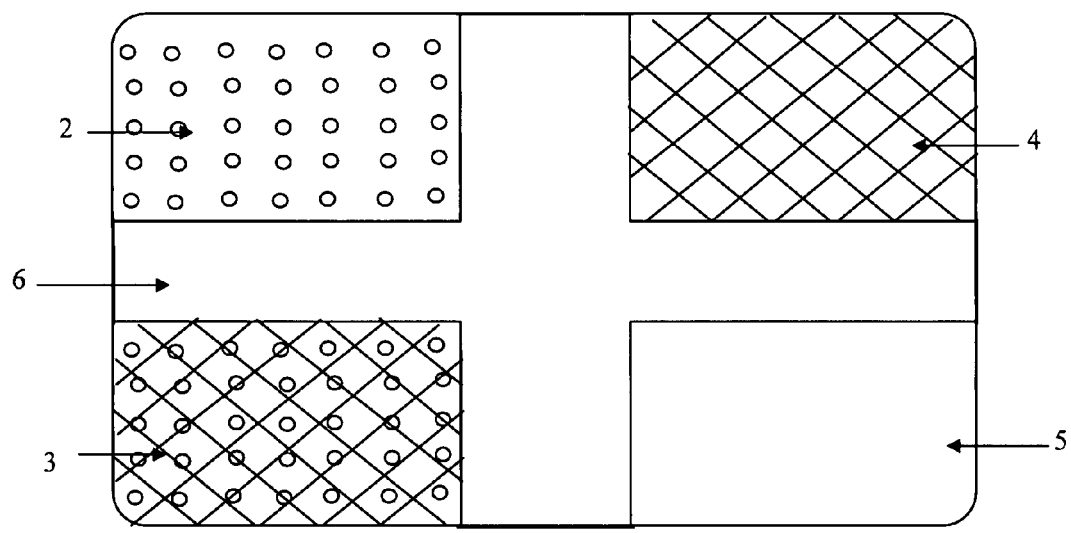
FIG. 6 is a top view of the third embodiment of the interdental cleaner

The interdental device 1 may have different surfaces or different cleaning substances combined with the zones 2-5 thickness, as show in FIG. 6. For example at least one zone may contain a tooth cleaning substance, a plaque removing substance, a teeth 10 whitening substance, flavor or breathe freshening substance in combination with a corrugated surfaces or any other surface that improve the removal entrained matter between teeth 10 make with fiber, plastic, paper or any other harmless material for teeth cleaning purposes. The substance can also be apart in a small bucket in which the user immerses the interdental cleaner device before applying it.

Figure 7:
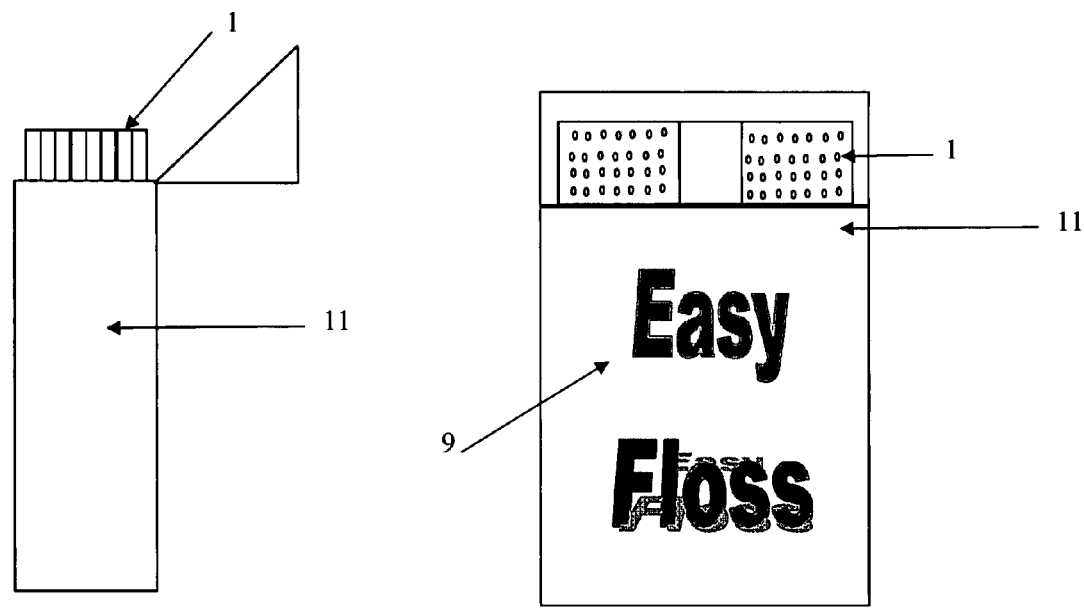
FIG. 7 is a casing for the interdental cleaner

The interdental device 1 can be made as a reusable or a non-reusable device; however the non-reusable or disposable is preferred for sanitary reasons. A package 11, as shown in FIG. 7, is provided for carrying several disposable interdental cleaner devices 1. The package 11 displays advertising matter 9 such as brand name or any other information.

Figure 8:
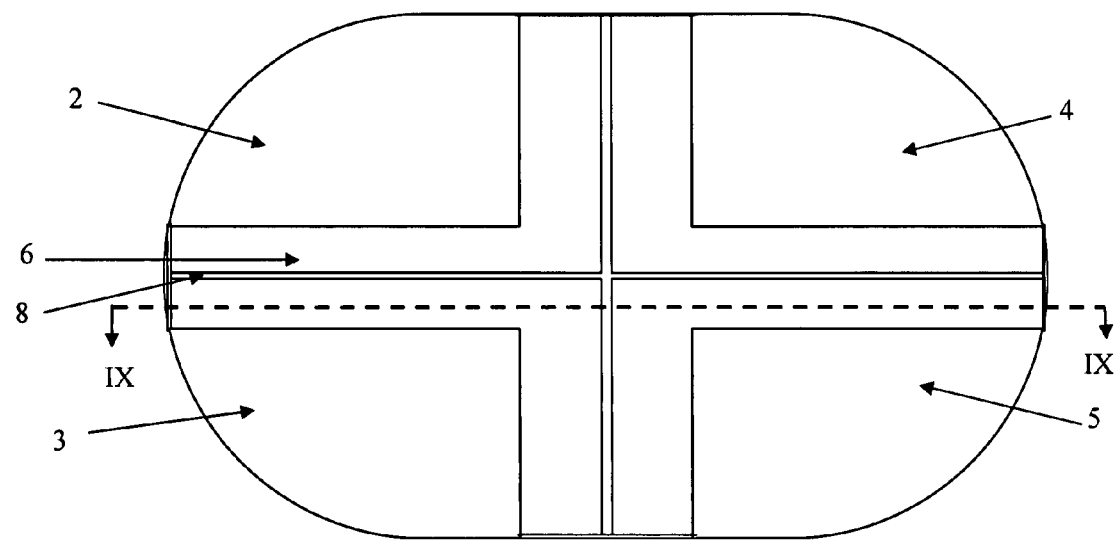
FIG. 8 is a top view of the third embodiment of the interdental cleaner
Figure 9:
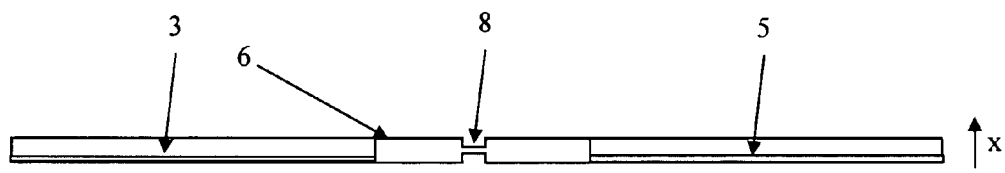
FIG. 9 is a cross section view on line IX-IX of the interdental cleaner
Figure 10:
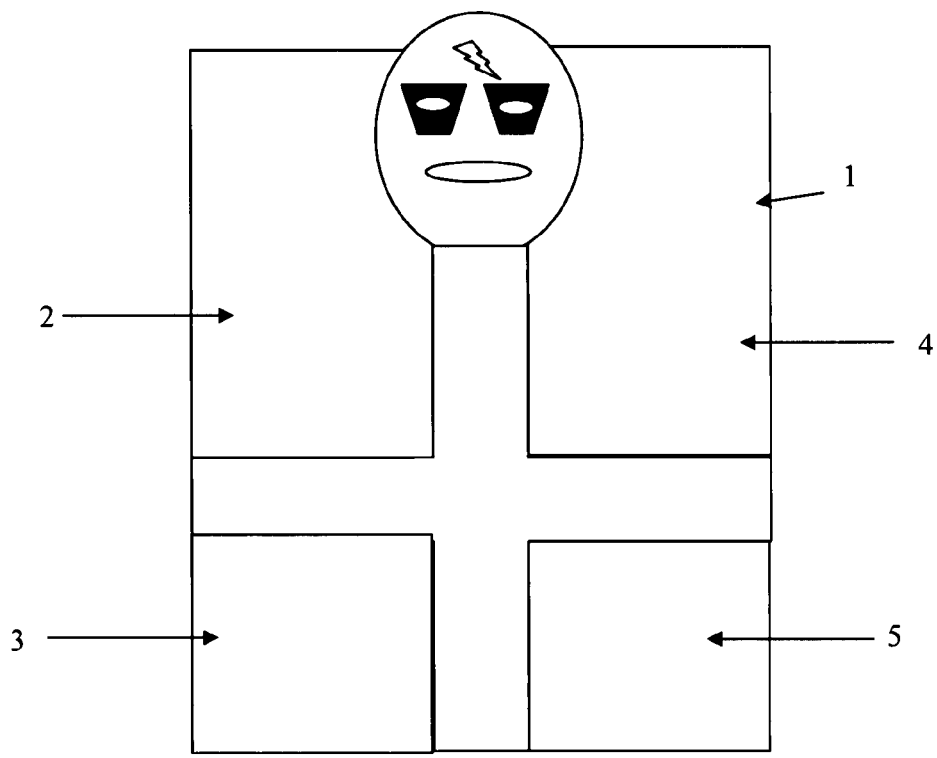
FIG. 10 is a top view of the interdental cleaner for Kids.

FIGS. 8 and 9 show a third embodiment of the present invention comprising four zones 2-5, wherein each zone has different thickness that can be combine with a particular surface and/or substance as mention before. In this case the interdental cleaner device 1 has a groove 8 as part of a frame 6. The groove 8 is use to reduce the thickness providing a breakable frame in order to detach each zone 2-5. FIG. 9 shows each zone at the distal end of the frame rather than the center of the frame in the axial x direction making the interdental cleaner device easier to manufacture. Also the frame thickness can be reduced if needed. The interdental cleaner 1 has a oval shape, however the shape can vary as long the structure is provided with at least more than one zone. It can be shaped to have a superhero or animal shape, as show in FIG. 10, which may be combine with the zones 2-5 having particular flavors in order to make it more attractive to the kids so they use the interdental device more often.

Figure 11:
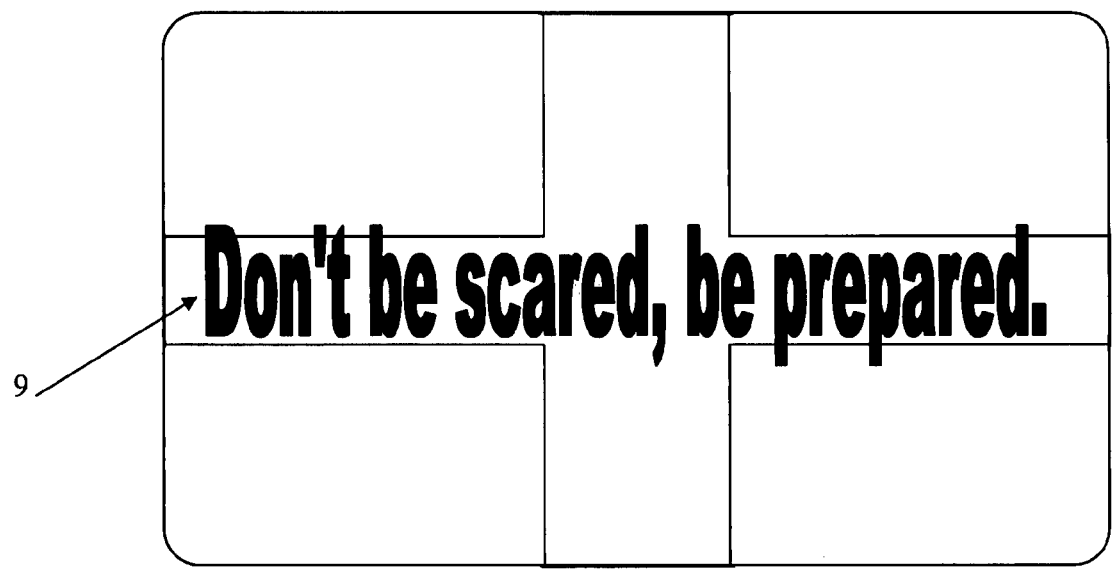
FIG. 11 is a top view of the interdental cleaner with advertisement.
Figure 12:
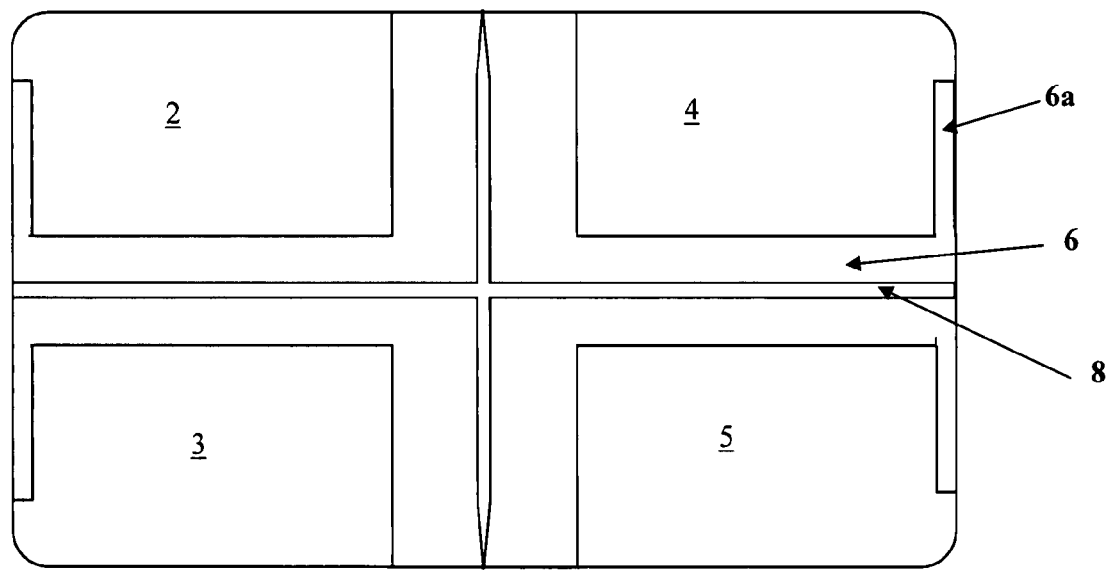
FIG. 12 is a top view of fourth embodiment of the interdental cleaner.
Figure 13:
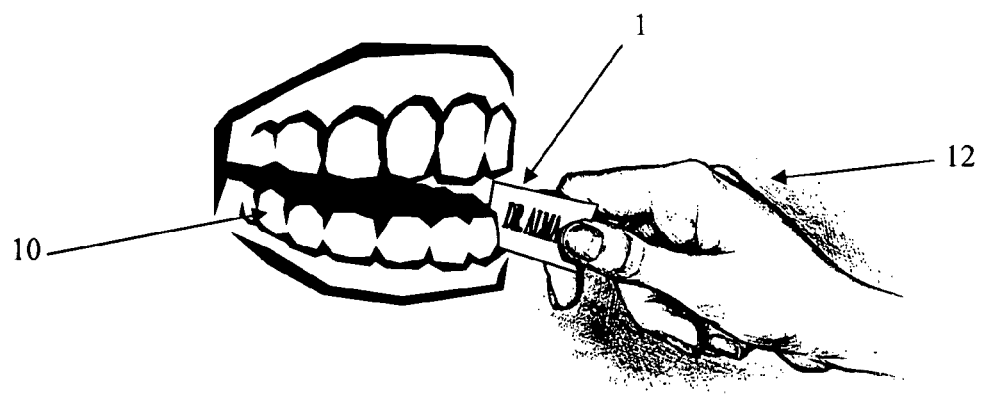
FIG. 13 is a view of applying the interdental cleaner.

As shown in FIG. 11, the interdental cleaner 1 can be used for displaying particular information such as announcements or any other information. As shown in figure 12, the frame 6, which provide rigidity to the zones 2-5, may include projections 6a extended at the outer surface of the zones 2-5 contacting each zone at least on three sides in order to provide a more rigid zone and/or reducing the frame thickness.

The interdental cleaner 1 can be used at anytime especially after eating in order to remove the food between teeth 10 or after brushing the teeth 10. The simplicity of the design provides a dental cleaning device that is easy to handle, especially for a kid or handicapped people, which not just removes the food between teeth 10 but also encourages thorough teeth 10 cleaning to prevent caries and inflammation of the gum.

The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

The invention claimed is:

1. An interdental cleaning device comprising:
   at least two cleaning zones, wherein each cleaning zone is a single structure comprising a cleaning zone perimeter which includes four sides, wherein said cleaning zone perimeter comprises a contacting perimeter zone and an outer surface, wherein said cleaning zone perimeter surrounds a uniform thickness zone,
   a breakable frame comprising a frame thickness, wherein said breakable frame is attached to said contacting perimeter zone supporting said cleaning zones and wherein said breakable frame is contacted with at least three sides of each of said cleaning zones,
   wherein each uniform thickness zone has different thickness, and
   wherein the frame thickness has a thickness greater than any cleaning zones thickness.

2. An interdental cleaning device according to claim 1, comprising four cleaning zones.

3. An interdental cleaning device according to claim 1, wherein said outer surface comprises a tapered portion, wherein said tapered portion is not covered by said breakable frame.

4. An interdental cleaning device according to claim 1, wherein said contacting perimeter zone comprises at least half of cleaning zone total perimeter and wherein said breakable frame contacts completely said contacting perimeter zone.

5. An interdental cleaning device according to claim 4, wherein the breakable frame contacts at least part of the outer surface.

6. An interdental cleaning device according to claim 1, wherein the cleaning zones are made by fiber, paper or plastic.

7. An interdental cleaning device according to claim 1, wherein the frame is materially different between each cleaning zones.

8. An interdental cleaning device according to claim 1, wherein said breakable frame has an animal or action figure shape.

9. An interdental cleaning device according to claim 1, wherein said breakable frame comprises grooves, wherein said grooves reduce the frame thickness providing detachable cleaning zones and wherein each detachable zone comprises a cleaning zone attached to a portion of the breakable frame.

10. An interdental cleaning device comprising:
a plurality of cleaning zones, wherein each cleaning zone is a single structure comprising a cleaning zone perimeter which includes four sides, wherein said cleaning zone perimeter comprises a contacting perimeter zone and an outer surface, wherein said outer surface comprises a tapered portion, wherein said cleaning zone perimeter surrounds a uniform thickness zone,
a breakable frame comprising a frame thickness, wherein said breakable frame is attached to said contacting perimeter zone supporting said cleaning zones and wherein said breakable frame is contacted with at least three sides of each of said cleaning zones,
wherein each uniform thickness zone has a different thickness, and
wherein the frame thickness has a thickness greater than any cleaning zones thickness.

11. An interdental cleaning device comprising:
a plurality of cleaning zones, wherein each cleaning zone is a single structure comprising a cleaning zone perimeter which includes four sides, wherein said cleaning zone perimeter comprises a contacting perimeter zone and an outer surface, wherein said cleaning zone perimeter surrounds a uniform thickness zone,
a breakable frame comprising a frame thickness and grooves, wherein said grooves reduce the frame thickness providing detachable cleaning zones and wherein each detachable zone comprises a cleaning zone attached to a portion of the breakable frame,
wherein said breakable frame is attached to said contacting perimeter zone supporting said cleaning zones and wherein said breakable frame is contacted with at least three sides of each of said cleaning zone,
wherein each uniform thickness zone has a different thickness, and
wherein the frame thickness has a thickness greater than any cleaning zones thickness.

* * * * *